US00PP09978P

United States Patent [19]

Svejda et al.

[11] Patent Number: Plant 9,978

[45] Date of Patent: Jul. 29, 1997

[54] SHRUB ROSE PLANT NAMED 'LAMBERT CLOSSE'

[75] Inventors: Felicitas J. Svejda, Nepean; Ian S. Ogilvie, Pointe Claire, both of Canada

[73] Assignee: Her Majesty the Queen in right of Canada, as represented by the Minister of Agriculture, Canada

[21] Appl. No.: 662,759

[22] Filed: Jun. 10, 1996

[51] Int. Cl.[6] ..... A01H 5/00

[52] U.S. Cl. ..... Plt./1

[58] Field of Search ..... Plt./1, 26, 27

*Primary Examiner*—Howard J. Locker

*Attorney, Agent, or Firm*—Burns, Doane, Swecker & Mathis, L.L.P.

[57] ABSTRACT

A new and distinct variety of shrub rose plant is provided which forms singly and in clusters attractive pink blossoms that tend to lighten somewhat when fully open. The new variety exhibits an upright and bushy growth habit with glossy foliage, and good winter hardiness. Resistance to powdery mildew and relatively good tolerance to blackspot have been observed. The new variety propagates well by the use of softwood stem cuttings, and is well adapted for growing as colorful ornamentation in the landscape.

2 Drawing Sheets

SUMMARY OF THE INVENTION

The new variety of shrub rose plant of the present invention was created by artificial pollination at the Central Experimental Farm, Ottawa, Ontario, Canada. The female parent (i.e., the seed parent) was 'Arthur Bell' (non-patented in the United States) and the male parent (i.e., the pollen parent) was 'John Davis' (non-patented in the United States). 'Arthur Bell' is a female fertile yellow Floribunda that was developed by McGredy in Northern Ireland. 'John Davis' is a climber rose selected from a cross *Rosa kordesii* and breeding line D08 that originated from a cross between the climber 'Red Dawn' (non-patented in the United States) and 'Suzanne' (non-patented in the United States). 'Suzanne' was a hybrid between *Rosa laxa* and *Rosa spinosissima*. The high degree of winter hardiness was derived through 'John Davis' from *Rosa kordesii* Wulff, *Rosa laxa* Retzius, and *Rosa spinosissima* L., which are recognized to be hardy species from Northern Europe and Asia.

it was found that the new variety of shrub rose plant of the present invention possesses the following combination of characteristics:

(a) exhibits an upright growth habit with attractive dark green glossy foliage,
(b) forms singly or in clusters attractive pink blossoms that tend to lighten when fully open,
(c) propagates well by the use of softwood cuttings,
(d) exhibits good winter hardiness, and
(e) is particularly well suited for growing as ornamentation in the landscape.

The rose plants can be grown well on their own roots out-of-doors without protection at L'Assomption, Quebec, Canada. The blossoms commonly appear repeatedly from June to September. Resistance to powdery mildew and relatively high tolerance to blackspot have been exhibited.

While the new variety resembles 'Alexander Mackenzie' (non-patented in the United States) somewhat, it can be readily distinguished by the presence of many more petals and by the configuration and coloration of the buds.

The new variety well meets the needs of the horticultural industry. It can be grown to advantage as attractive ornamentation in parks, gardens, public areas, and residential landscapes. It is particularly well suited for growing in the landscape.

The characteristics of the new variety have been found to be homogenous and stable and have been shown to be strictly transmissible by asexual propagation by the rooting of softwood stem cuttings conducted a L'Assomption, Quebec, Canada.

The new variety has been named 'Lambert Closse'.

BRIEF DESCRIPTION OF THE PHOTOGRAPHS

The accompanying photographs show, as nearly true as it is reasonably possible to make the same in color illustrations of this character, typical specimens of plants and plant parts of the new variety. The rose plants of the new variety described herein were approximately 5 to 6 years of age and were photographed while growing on their own roots at L'Assomption, Quebec, Canada.

FIG. 1—illustrates a typical flowering plant of the new variety while growing in the landscape. The upright growth habit, abundant foliage, and attractive pink blossoms are apparent.

FIG. 2—illustrates typical blossoms and glossy dark green foliage of the new variety.

DETAILED DESCRIPTION

Figure 1:
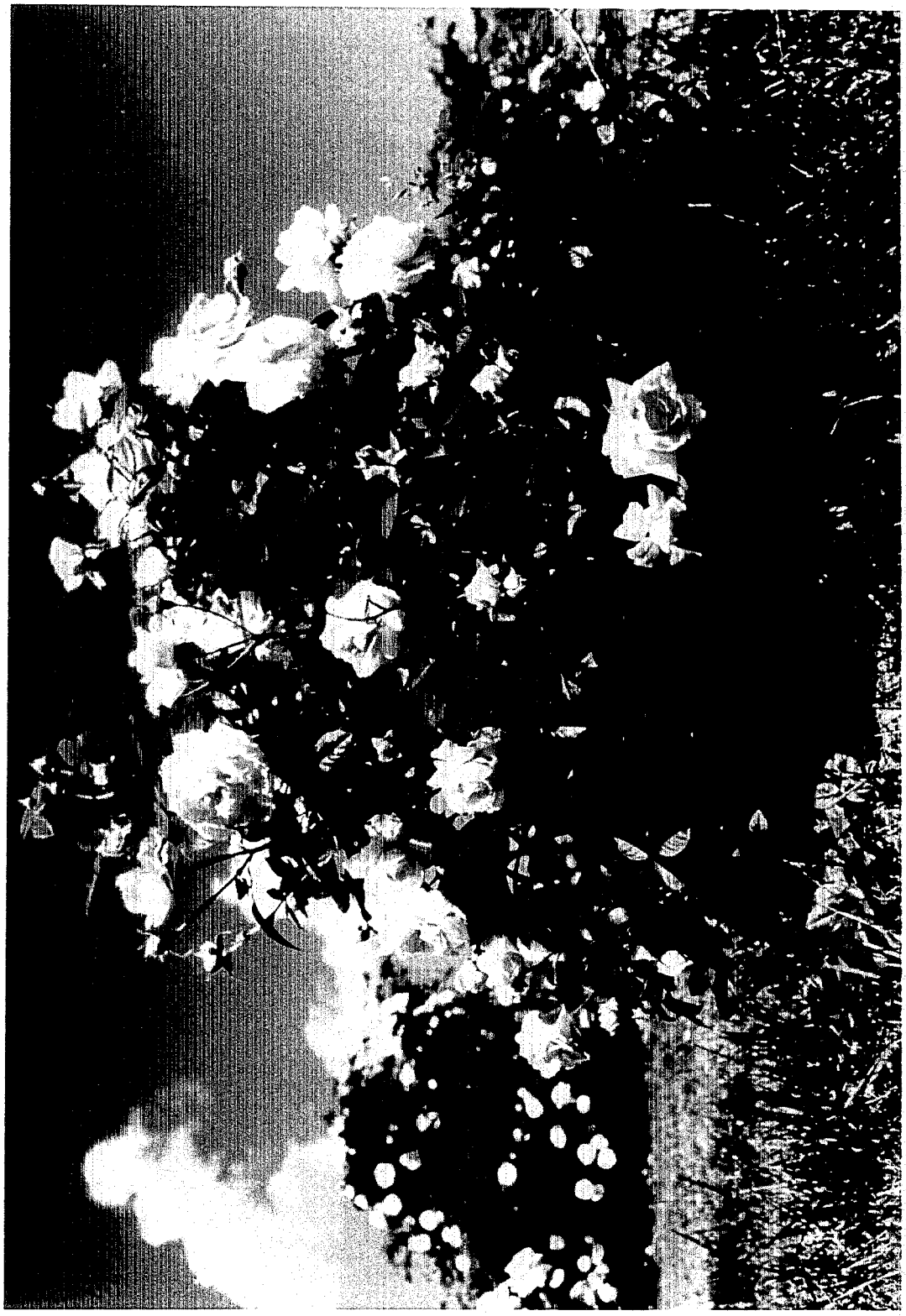
Figure 2:
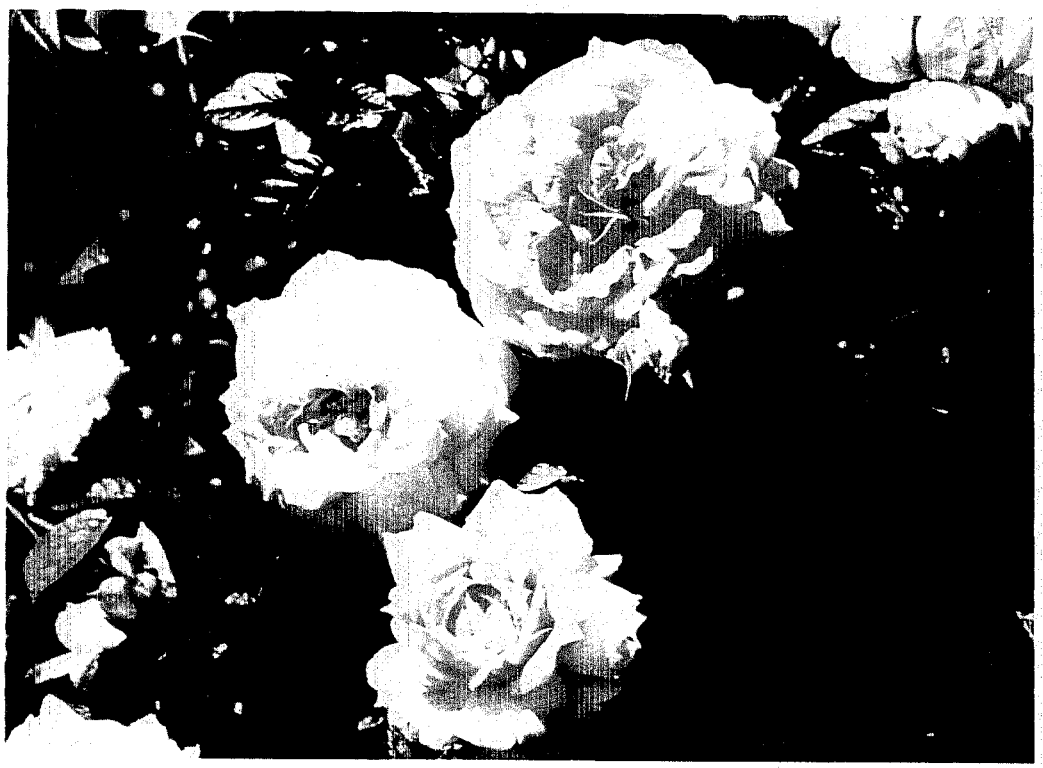

The chart used in the identification of colors is that of The Royal Horticultural Society (R.H.S. Colour Chart). Common color terms are to be accorded their ordinary dictionary significance. The description is based on the observation of 5 to 6 year-old plants of the new variety while being grown outdoors at L'Assomption, Quebec, Canada.

Class: Shrub.

Plant:

*Height.*—A five year-old plant commonly assumes a height of approximately 0.85 m.

*Width.*—A five year-old plant commonly assumes a width of approximately 0.85 m.

*Habit.*—Upright and bushy.

Thorns:

*Quantity.*—Approximately 8±2 thorns per 100 mm. of stem on average.

Leaves: Compound and pinnate.

*Leaflets.*—Number: commonly 3, 5 or 7. Frequency: abundant. Shape: ovate and acuminate. Margins: dentate. Size: approximately 45 mm. in length on average and approximately 26 mm. in width on average. Texture: leathery. General appearance: dark green, and glossy.

*Color.*—Adult foliage: dark green, Yellow-Green Group 146A on upper surface and Yellow-Green Group 147C on under surface.

Inflorescence:

*Number of flowers.*—Singly or in clusters of 2 to 3.

*Peduncle.*—Erect.

*Buds.*—Shape: hybrid-tea like and ovoid before the opening of the sepals, as shown in FIG. 1. Color upon opening: the outer petals are deep pink.

*Flower.*—Shape: assume a more flattened configuration when fully open (as illustrated). Diameter: approximately 80 mm. on average. Color (when blooming): medium pink, Red Group 55B on the upper surface and Red Group 55D on the under surface. Initially the blossoms commonly display a blend of medium pink coloration that tends to fade to pale pink when fully open. At the base the petals exhibit a yellow spot of Yellow-Green Group 1A. Fragrance: slight. Petal number: approximately 53±4 on average. Petal drop: petals tend to detach fairly clearly. Fertility: flowers commonly possess a low level of fertility and only occasional hips are formed upon open-pollination that are ovoid in shape. Lasting quality: the blossoms commonly last 3 to 5 days when cut and placed in a vase and generally last longer on the plant. The blossom life is influenced by temperature and other environmental conditions that are encountered.

Development:

*Vegetation.*—Good vigor.

*Blossoming.*—Good repeat blooming from June to September that closely resembles that of a Hybrid Tea variety.

*Hardiness.*—Has survived test winters to −35° C. without protection except for natural snow with only slight winter injury. Only light pruning of dead wood commonly is required following normal winters.

*Resistance to diseases.*—Resistance to powdery mildew [*Sphaerotheca pannosa* (Wallr. ex Fr.) Lev.] and a relatively good tolerance to blackspot (*Diplocarpon rosae* Wolf.) have been observed.

*Preferred mode of propagation.*—The use of softwood cuttings to produce self-rooted plants is recommended. For instance, softwood cuttings taken at the bud stage can be dipped in rooting powder (e.g., Stimroot No. 2, 0.4 percent indolebutyric acid of Plant Products, Bramalea, Ontario, Canada) and placed under mist for 3 to 4 weeks at 20° to 25° C. ambient temperature.

We claim:

1. A new and distinct variety of shrub rose plant characterized by the following combination of characteristics:

(a) exhibits an upright growth habit with attractive dark green glossy foliage,
(b) forms singly or in clusters attractive pink blossoms that tend to lighten when fully open,
(c) propagates well by the use of softwood cuttings,
(d) exhibits a good winter hardiness, and
(e) is particularly well suited for growing as ornamentation in the landscape;

substantially as herein shown and described.

* * * * *